(12) United States Patent
Kim et al.

(10) Patent No.: US 11,839,285 B2
(45) Date of Patent: *Dec. 12, 2023

(54) COSMETICS HAVING IMPREGNATION MEMBER WITH RECESSED PATTERN FORMED ON SURFACE THEROF BY LASER PROCESSING

(71) Applicant: AMOREPACIFIC CORPORATION, Seoul (KR)

(72) Inventors: Jun Young Kim, Seoul (KR); Ju Ho Kim, Seoul (KR)

(73) Assignee: AMOREPACIFIC CORPORATION, Seoul (KR)

( * ) Notice: Subject to any disclaimer, the term of this patent is extended or adjusted under 35 U.S.C. 154(b) by 446 days.

This patent is subject to a terminal disclaimer.

(21) Appl. No.: 15/777,579

(22) PCT Filed: Nov. 23, 2016

(86) PCT No.: PCT/KR2016/013507
§ 371 (c)(1),
(2) Date: May 18, 2018

(87) PCT Pub. No.: WO2017/090962
PCT Pub. Date: Jun. 1, 2017

(65) Prior Publication Data
US 2020/0008556 A1    Jan. 9, 2020

(30) Foreign Application Priority Data
Nov. 24, 2015   (KR) ........................ 10-2015-0164374
Aug. 29, 2016   (KR) ........................ 10-2016-0109742

(51) Int. Cl.
*A45D 33/24*        (2006.01)
*A45D 33/00*        (2006.01)
(Continued)

(52) U.S. Cl.
CPC ........... *A45D 33/24* (2013.01); *A45D 33/006* (2013.01); *A61K 8/022* (2013.01); *A61Q 1/12* (2013.01)

(58) Field of Classification Search
CPC ...... A45D 33/34; A45D 33/24; A45D 33/006; A45D 34/04; A45D 33/02; A61K 8/0216; A61K 8/022
(Continued)

(56) References Cited

U.S. PATENT DOCUMENTS 8,585,953 B2 * 11/2013 Caprarotta ............. A61K 8/022
                                                                    264/319
2003/0104036 A1 * 6/2003 Gregoire ................ D04H 1/495
                                                                    424/443
(Continued)

FOREIGN PATENT DOCUMENTS

CA        2804298 A1 *  9/2012  ............ A61Q 17/04
JP   2009201833 A   *  9/2009
(Continued)

OTHER PUBLICATIONS

Clarivate Analytics copywritten translation of KR200476594, publication date Mar. 16, 2015 (Year: 2015).*

*Primary Examiner* — Jacqueline T Johanas
*Assistant Examiner* — Sarah Woodhouse
(74) *Attorney, Agent, or Firm* — Heedong Chae; Lucem, PC

(57) ABSTRACT

A cosmetic container including an impregnation member having the surface intaglio-patterned by laser beam machining is provided. The surface of the impregnation member is heated and burned by a laser to form an intaglio-pattern, and an intaglio-pattern part having the intaglio-pattern is formed with a width of 0.1 mm to 5.0 mm so that the intaglio-pattern part formed by the laser is maintained in the open cell structure and has the large discharge surface area, so a user (Continued)

easily adjusts an amount of discharged cosmetic material according to force applied to the impregnation member and use the cosmetic material. The cosmetic container includes an outer container having an open upper portion, an outer container lid coupled to the outer container, an inner container mounted inside the outer container, the impregnation member in the inner container and impregnated with cosmetic material and an inner container lid hinged with the inner container.

8 Claims, 7 Drawing Sheets

(51) Int. Cl.
  *A61K 8/02* (2006.01)
  *A61Q 1/12* (2006.01)
(58) Field of Classification Search
  USPC .......................................... 132/300; 264/400
  See application file for complete search history.

(56) References Cited

U.S. PATENT DOCUMENTS

| | | | | |
|---|---|---|---|---|
| 2007/0277844 | A1* | 12/2007 | Gueret | A45D 34/04 |
| | | | | 132/320 |
| 2011/0247648 | A1* | 10/2011 | Ikeda | A61F 13/2077 |
| | | | | 132/320 |
| 2012/0286441 | A1* | 11/2012 | Johnson | A61K 8/34 |
| | | | | 264/36.1 |
| 2014/0341959 | A1* | 11/2014 | Choi | A45D 34/00 |
| | | | | 424/401 |
| 2014/0345639 | A1* | 11/2014 | Samain | A45D 33/006 |
| | | | | 132/200 |
| 2016/0051452 | A1* | 2/2016 | Nishizawa | A61K 8/0208 |
| | | | | 424/401 |
| 2016/0157585 | A1* | 6/2016 | Kang | A45D 40/0068 |
| | | | | 220/259.2 |
| 2018/0015005 | A1* | 1/2018 | Cho | A45D 34/00 |
| 2018/0318179 | A1* | 11/2018 | Kang | A61K 8/064 |

FOREIGN PATENT DOCUMENTS

| | | | | |
|---|---|---|---|---|
| JP | 2010-280788 A | | 12/2010 | |
| KR | 10-2013-0116194 A | | 10/2013 | |
| KR | 10-1385652 B1 | | 5/2014 | |
| KR | 10-2015-0073852 A | | 7/2015 | |
| KR | 20-2015-0003870 U | | 10/2015 | |
| KR | 2020150003870 | * | 10/2015 | ............. A45D 34/04 |
| KR | 10-1566803 B1 | | 11/2015 | |
| KR | 101566803 B1 | * | 11/2015 | ............. B65D 83/00 |
| KR | 2020150003870 | * | 11/2015 | ............. A45D 34/04 |
| WO | WO-2014005265 A1 | * | 1/2014 | ............. A45D 40/00 |
| WO | WO-2015060473 A1 | * | 4/2015 | ............. A45D 34/04 |
| WO | WO-2017138724 A1 | * | 8/2017 | ............. A45D 33/36 |

* cited by examiner

COSMETICS HAVING IMPREGNATION MEMBER WITH RECESSED PATTERN FORMED ON SURFACE THEROF BY LASER PROCESSING

CROSS-REFERENCE TO RELATED APPLICATION

This application claims the benefit of Korean application No. 10-2015-0164374, filed on Nov. 24, 2015 and application No. 10-2016-0109742, filed on Aug. 29, 2016, the disclosure of which is incorporated herein by reference.

TECHNICAL FIELD

The present invention relates to a cosmetic container including an impregnation member having a surface intaglio-patterned by laser beam machining, and more particularly to a cosmetic container including an impregnation member having a surface intaglio-patterned by laser beam machining, in which a surface of the impregnation member is heated and burned by a laser to form an intaglio-pattern, and an intaglio-pattern part having the intaglio-pattern is formed with a width in the range of 0.1 mm to 5.0 mm so that the intaglio-pattern part formed by a laser is maintained in an open cell structure and has a large discharge surface area, so a user can easily adjust an amount of discharged cosmetic material according to force applied to the impregnation member and use the cosmetic material.

BACKGROUND ART

Cosmetics refer to compositions which are used for a human body in order to add charming of the human body by making the human body clean and beautiful, to change the appearance of the human body into being brighter, to maintain skin or hair in a healthy state, or to enhance the skin or the hair, and to exert slight influence on the human body.

In general, the cosmetics are obtained by mixing an emulsifier, such as a surfactant, with cosmetic material having a different formulation, and classified into water-in-oil type and oil-in-water type cosmetics depending on the bonding structures of water-phase and oil-phase material.

The water-in-oil type cosmetic material is obtained by bonding an oil-phase material to an outer portion of the water-phase material. The water-in-oil type cosmetic material contains a large amount of oil, and thus slowly absorbed in the skin, which makes a user feel heavy.

However, the water-in-oil type cosmetic material has a long-lasting effect higher than that of the oil-in-water type cosmetic material. Cosmetics required with a higher long-lasting effect are prepared using the oil-in-water type cosmetic material so that water resistance to sweat or water may be enhanced.

In order to overcome the disadvantages of sticky and heavy feeling for the water-in-oil type cosmetic material, the cosmetics are prepared with lower viscosity. However, the lower-viscosity water-in-oil type cosmetics are divided into water-phase material, which is an inner material, and an oil-phase material, which is an outer material, when being stored in a container for a long time during the distribution. Accordingly, a user must inconveniently use the water-in-oil type cosmetics by shaking a cosmetic container so that the water-phase material and the oil-phase material are mixed with each other.

In order to solve the above problem, as shown in FIG. 1, the applicant of the present invention has developed a product of a compact container including an impregnation member 1 impregnated with water-in-oil type contents having lower viscosity as disclosed in Korean Patent Registration No. 10-1159877.

However, according to the related art, cosmetic contents are fully filled in the impregnation member 1 when a user first uses cosmetics. Accordingly, even if a user presses the impregnation member 1 by less force, an excessive amount of contents is applied to a puff so that the cosmetics may be wasted.

In order to solve the above problems, as shown in FIG. 2, the applicant of the present invention is issued with Korean Patent Registration No. 10-1566803. According to the patent, the surface of an impregnation member 2 is pressed onto a heated metallic mold having intaglio and embossment patterns and molten, so that intaglio and embossment patterns are formed on the surface of the impregnation member 2. The open cell structure of the surface of the impregnation member 2 is molten and deformed to a ½ or less sized open cell structure. Accordingly, if a user brings a puff into contact with the impregnation member 2 for the use of contents, the contents are discharged from the impregnation member 2 bit by bit, thereby preventing the contents from being wasted as an excessive amount of contents are applied to the puff.

However, according to the related art, the surface of the impregnation member 2 is pressed onto a metallic mold heated through a thermoforming technique by a punch and molten so that intaglio and embossment patterns are formed on the surface of the impregnation member 2. Accordingly, the open cell structure of the surface of the impregnation member 2 is molten and becomes a close cell structure. Accordingly, the cosmetic material impregnated into the impregnation member 2 is not sufficiently applied to the puff, so that makeup may be difficult.

In addition, since the intaglio and embossment patterns are not freely and delicately realized on the surface of the impregnation member 2, so that the impregnation member 2 may not be manufactured in various designs.

DISCLOSURE

Technical Problem

The present invention is made in order to solve the above problem, and an object of the present invention is to provide a cosmetic container including an impregnation member having a surface intaglio-patterned by laser beam machining, in which a surface of the impregnation member is heated and burned by a laser to form an intaglio-pattern, and an intaglio-pattern part having the intaglio-pattern is formed with a width in the range of 0.1 mm to 5.0 mm so that the intaglio-pattern part formed by the laser is maintained in an open cell structure and has a large discharge surface area, so a user can easily adjust an amount of discharged cosmetic material according to force applied to the impregnation member and use the cosmetic material.

Another object of the present invention is to provide a cosmetic container including an impregnation member having a surface intaglio-patterned by laser beam machining, in which a surface of the impregnation member is delicately intaglio-patterned by a laser, so that free and delicate patterns can be realized, and various and delicate logos can be formed, thereby maximizing the aesthetics of the impregnating member.

Still another object of the present invention is to provide a cosmetic container including an impregnation member having a surface intaglio-patterned by laser beam machining, in which an intaglio-pattern can be easily formed on the surface of the impregnation member, so that variously-shaped intaglio-patterns can be easily formed, thereby providing patterns for consumers according to the preferences of the consumers.

Technical Solution

In order to accomplish the objects of the present invention, there is provided an outer container (10) having an upper portion that is open, an outer container lid (20) coupled to one side of the outer container (10), an inner container (30) mounted inside the outer container (10), the impregnation member (40) mounted in the inner container (30) and impregnated with cosmetic material, and an inner container lid (60) hinged with one side of the inner container (30) to be open or closed. The impregnation member (40) includes an intaglio-pattern part (42) having an intaglio-pattern formed as the surface (41) is burned by a laser.

In addition, a fixing member (50) is further coupled to an upper end of the inner container (30) to prevent the impregnation member (40) from deviating out of the inner container (30).

Further, the intaglio-pattern part (42) is provided in a form of a pattern or a logo on the surface (41) of the impregnation member (40).

Further, the intaglio-pattern part (42) is formed on the surface (41) of the impregnation member (40) and formed in a form of multiple parallel lines, or in a form of a lattice pattern or an oblique pattern formed as the multiple parallel lines cross each other.

In addition, the intaglio-pattern part (42) has a width (w) in a range of 0.1 mm to 5.0 mm, and a depth (d) in a range of 0.2 mm to 8.0 mm.

Further, the intaglio-pattern part (42) is maintained in an open cell structure and has a section formed in an inverted triangular shape.

Advantageous Effect

As described above, according to the present invention, in the cosmetic container including the impregnation member having the surface intaglio-patterned by laser beam machining, the surface of the impregnation member is heated and burned by the laser to form the intaglio-pattern, and the intaglio-pattern part having the intaglio-pattern is formed with a width in the range of 0.1 mm to 5.0 mm so that the intaglio-pattern part formed by the laser is maintained in the open cell structure and has the large discharge surface area, so a user can easily adjust an amount of discharged cosmetic material according to force applied to the impregnation member and use the cosmetic material.

In addition, according to the present invention, in the cosmetic container including the impregnation member having the surface intaglio-patterned by laser beam machining, the surface of the impregnation member can be delicately intaglio-patterned by a laser, so that free and delicate patterns can be realized, and various and delicate logos can be formed, thereby maximizing the aesthetics of the impregnating member.

Further, according to the present invention, in the cosmetic container including the impregnation member having the surface intaglio-patterned by laser beam machining, the intaglio-pattern can be easily formed on the surface of the impregnation member, so that variously-shaped intaglio-patterns can be easily formed, thereby providing patterns for consumers according to the preferences of the consumers.

BEST MODE

Mode for Invention

Hereinafter, a cosmetic container including an impregnation member having a surface intaglio-patterned by laser beam machining according to one embodiment of the present invention will be described with reference to accompanying drawings.

Figure 1:
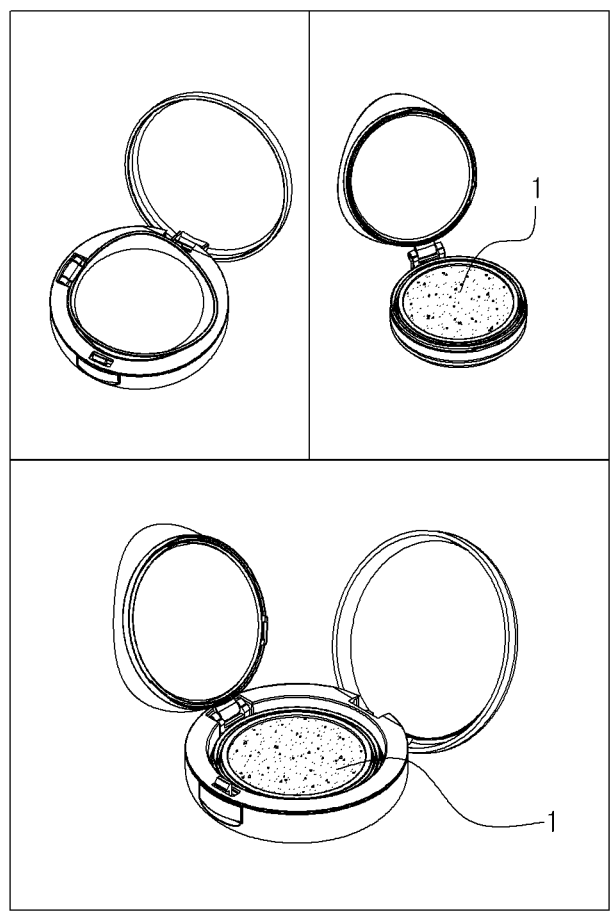
FIGS. 1 and 2 are perspective views showing cosmetic containers mounted therein with conventional impregnation members.
Figure 2:
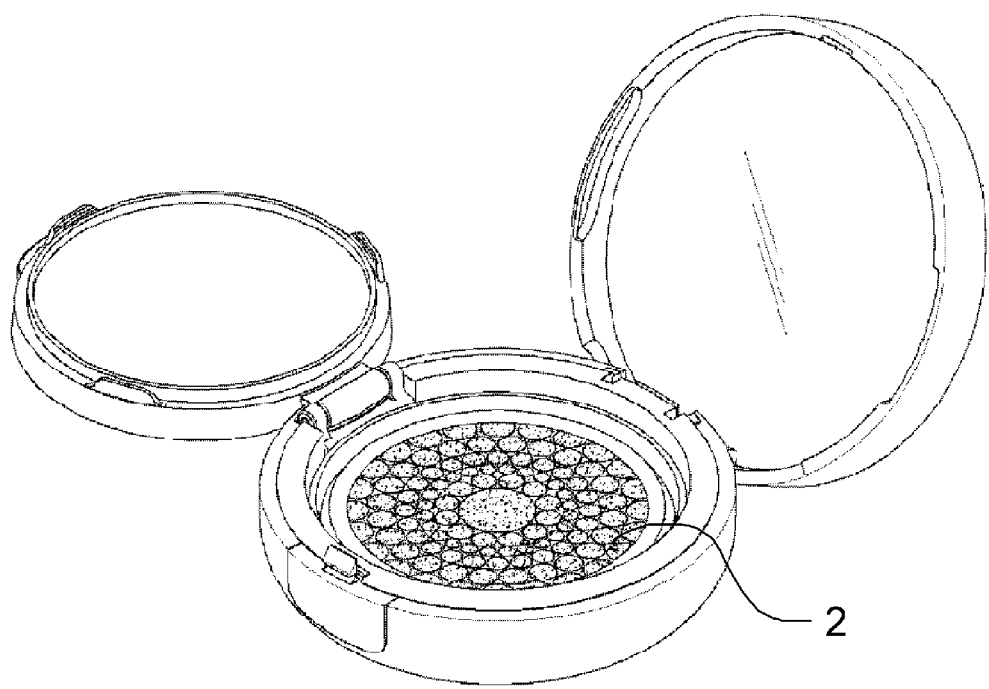
Figure 3:
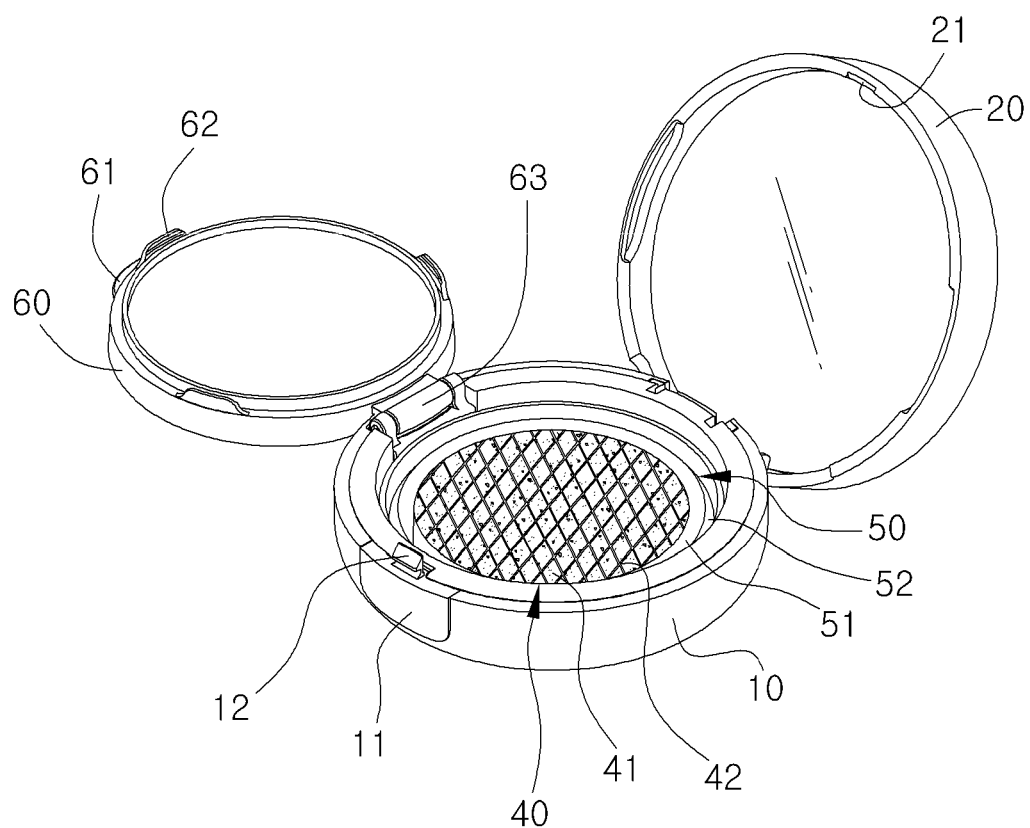
FIG. 3 is a perspective view showing a cosmetic container including an impregnation member having a surface intaglio-patterned by laser beam machining according to one embodiment of the present invention.
Figure 4:
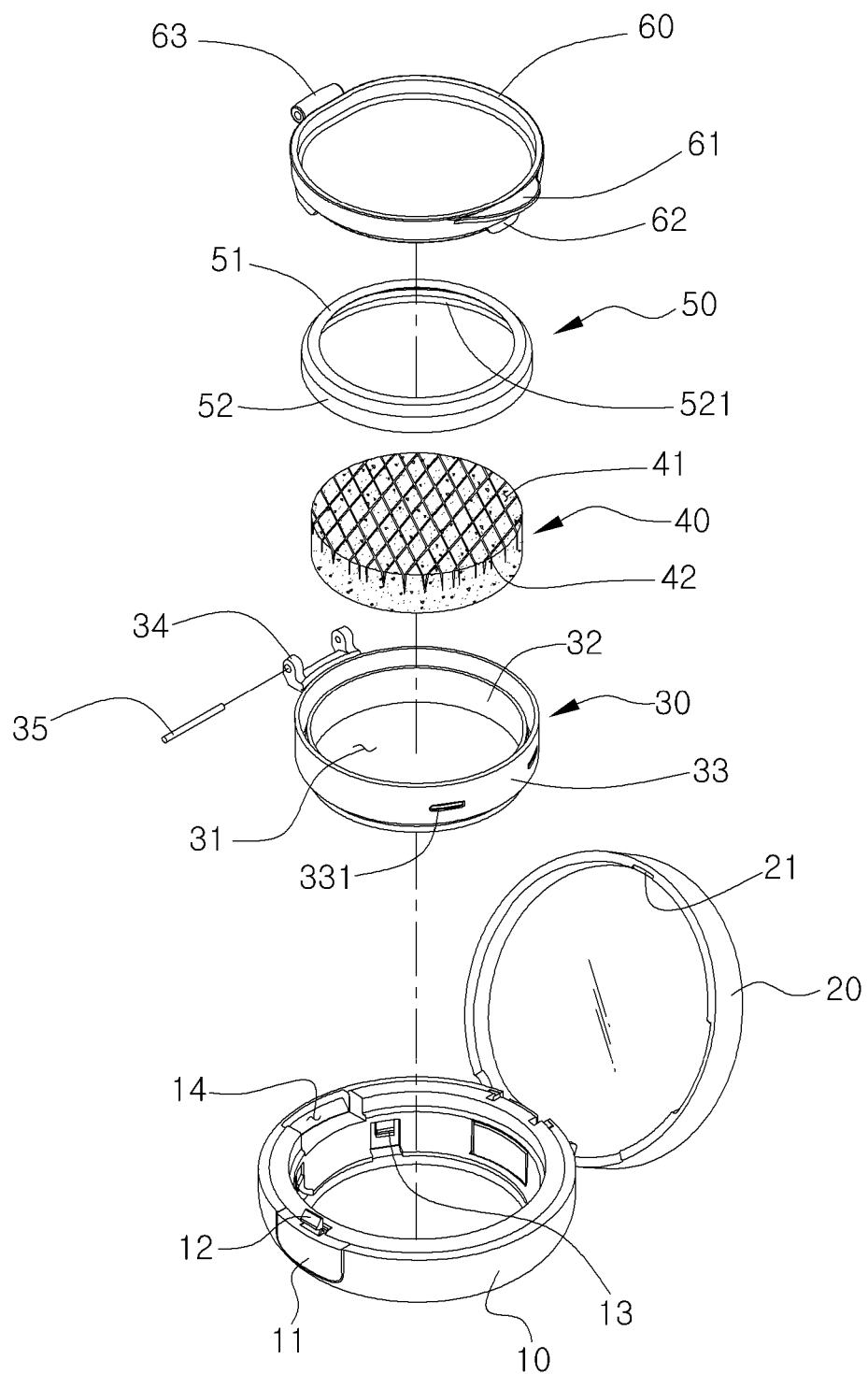
FIG. 4 is an exploded perspective view showing the cosmetic container including the impregnation member having the surface intaglio-patterned by laser beam machining according to one embodiment of the present invention.
Figure 5:
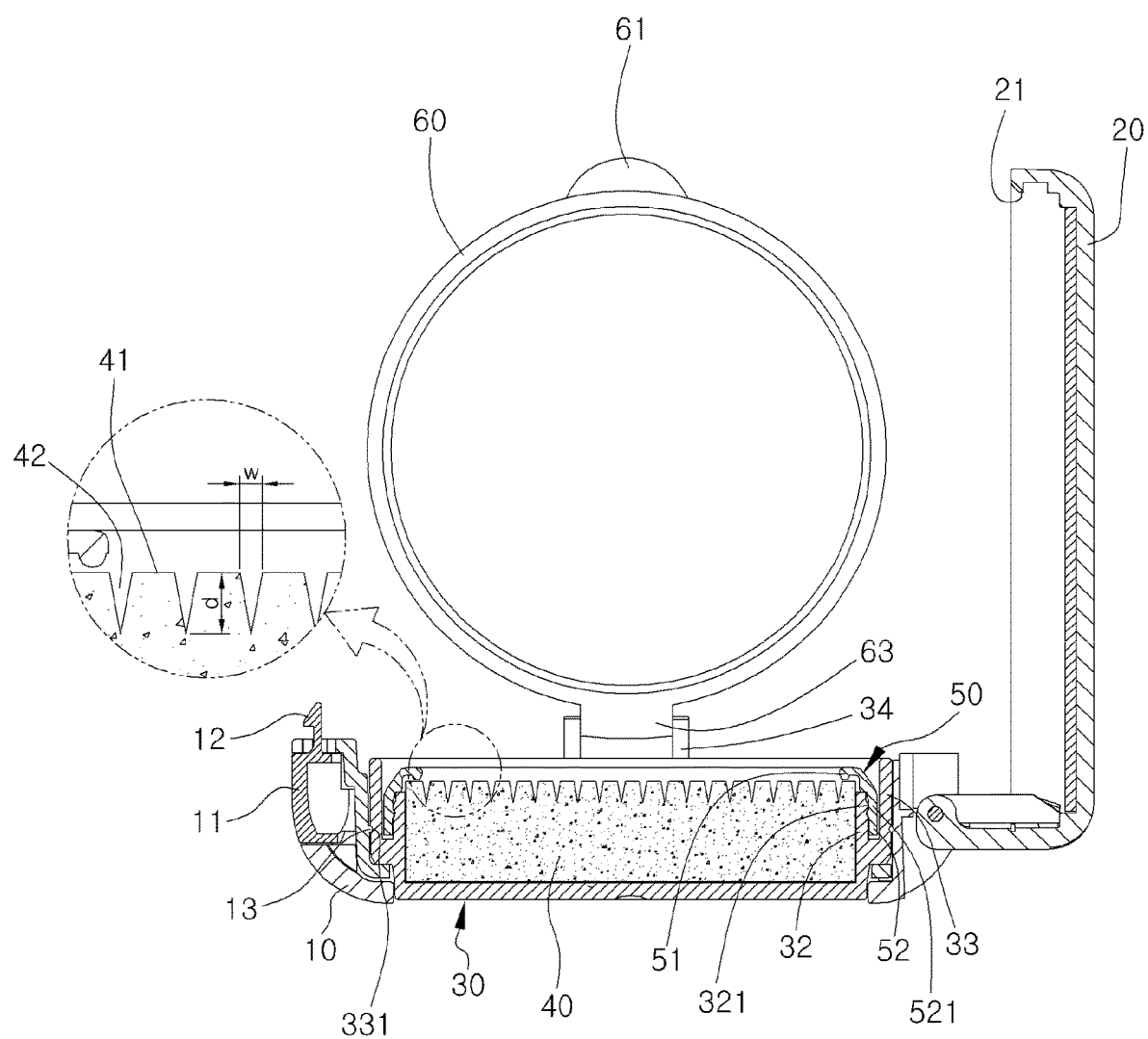
FIG. 5 is a sectional view showing the cosmetic container including the impregnation member having the surface intaglio-patterned by laser beam machining according to one embodiment of the present invention.
Figure 6:
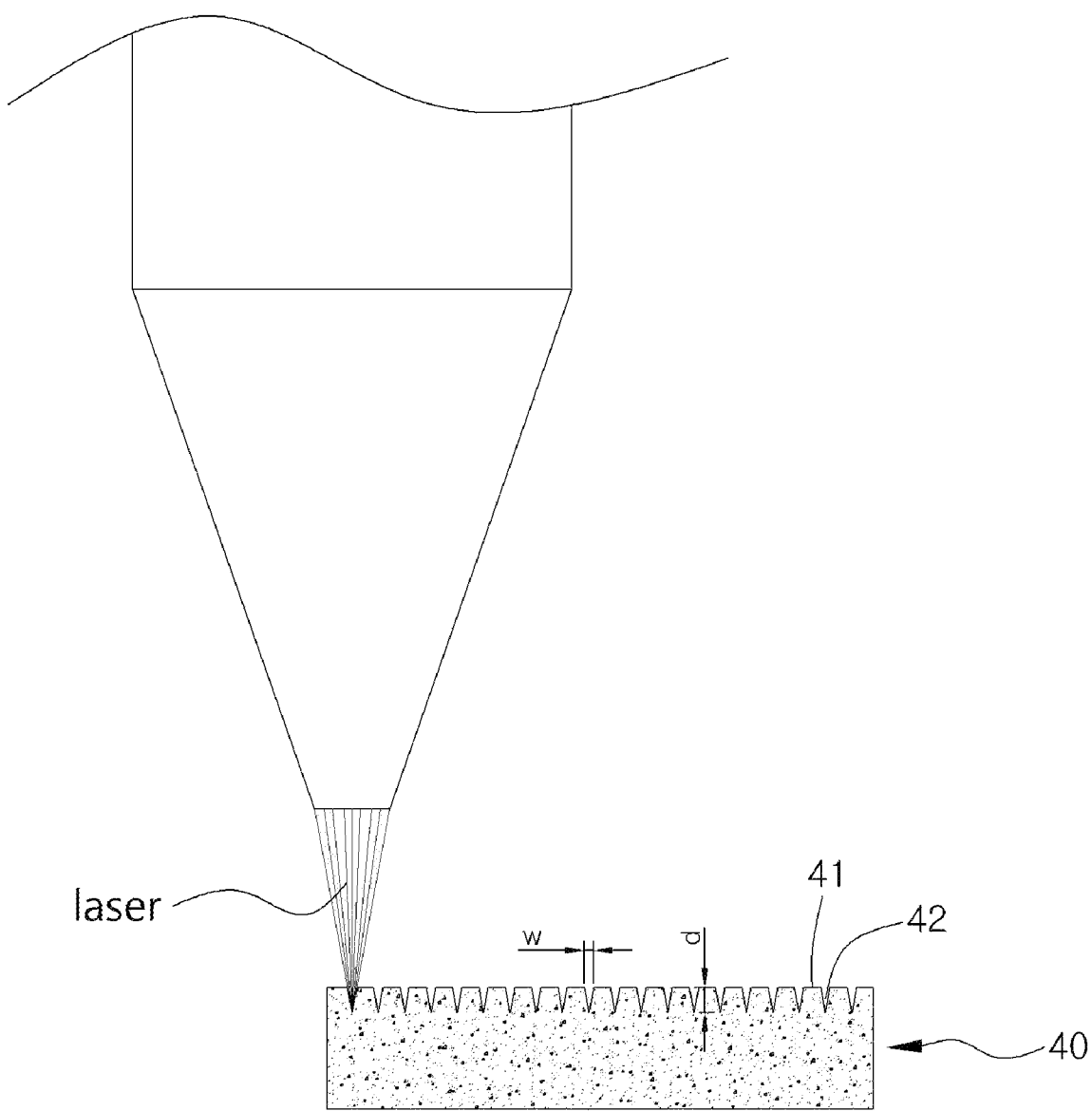
FIG. 6 is a sectional view showing a laser machining state for the impregnation member received in the cosmetic container including the impregnation member having the surface intaglio-patterned by laser beam machining according to one embodiment of the present invention.
Figure 7:
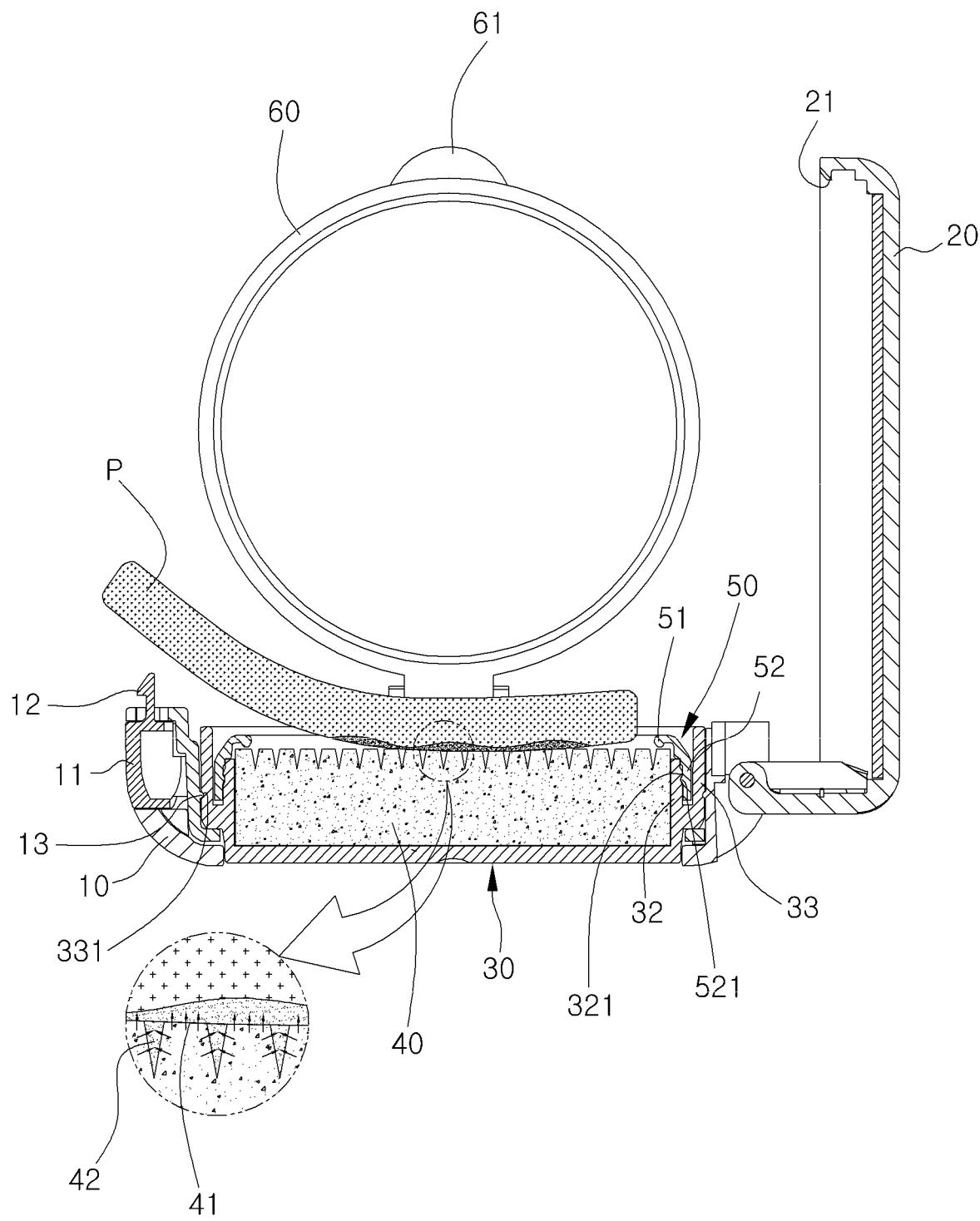
FIG. 7 is a sectional view showing a pressing state for the impregnation member in the cosmetic container including the impregnation member having the surface intaglio-patterned by laser beam machining according to one embodiment of the present invention.

FIG. 3 is a perspective view showing a cosmetic container including an impregnation member having a surface intaglio-patterned by laser beam machining according to one embodiment of the present invention. FIG. 4 is an exploded perspective view showing the cosmetic container including the impregnation member having the surface intaglio-patterned by laser beam machining according to one embodiment of the present invention. FIG. 5 is a sectional view showing the cosmetic container including the impregnation member having the surface intaglio-patterned by laser beam machining according to one embodiment of the present invention. FIG. 6 is a sectional view showing a laser machining state for the impregnation member received in the cosmetic container including the impregnation member having the surface intaglio-patterned by laser beam machining according to one embodiment of the present invention. FIG. 7 is a sectional view showing a pressing state for the impregnation member in the cosmetic container including the impregnation member having the surface intaglio-patterned by laser beam machining according to one embodiment of the present invention.

According to the present invention, in the cosmetic container including an impregnation member having a surface intaglio-patterned by laser beam machining, an intaglio-pattern part 42 having an intaglio-pattern is formed, in which the intaglio-pattern is formed as the surface 41 of the impregnation member 40 is burned by a laser, and the impregnation member 40 having the intaglio-pattern part 42 formed on the surface 41 thereof is impregnated with cosmetic material.

The cosmetic material impregnated into the impregnation member 40 may be a gel-phase foundation containing a sunscreen.

In addition, according to the present invention, the cosmetic container including the impregnation member having the surface intaglio-patterned by laser beam machining includes an outer container 10 having an upper portion that is open, an outer container lid 20 coupled to one side of the outer container 10, an inner container 30 mounted inside the outer container 10, the impregnation member 40 mounted in the inner container 30 and impregnated with cosmetic material, and an inner container lid 60 hinged with one side of the inner container 30 to be open or closed. The impregnation member 40 includes the intaglio-pattern part 42 having the intaglio-pattern formed as the surface 41 is burned by a laser.

The outer container 10 is provided at one side thereof with a pressing button 11 including a locking step 12 and provided at a side thereof, which faces the pressing button 11, with a hinge to be hinged with the outer container lid 20. The outer container 10 is provided on an inner peripheral surface thereof with a coupling protrusion 13, and provided in an inner circumference thereof with a hinge bracket mounting groove 14.

The pressing button 11 may be separated from a locking protrusion 21 of the outer container lid 20 as the locking step 12 extending upward from the pressing button 11 is easily retracted by the pressing operation of the user.

The coupling protrusion 13 is coupled to a coupling groove 331 formed in an outer peripheral surface of an outer wall 33 of the inner container 30.

The hinge bracket 34 of the inner container 30 is inserted and mounted into the hinge bracket mounting groove 14.

The outer container lid 20 covers an upper portion of the outer container 10, and is hinged with the outer container 10 to open or close the outer container 10.

The locking protrusion 21 is formed at one side of the outer container lid 20 and has a protrusion shape corresponding to the locking step 12 of the outer container 10.

The inner container 30 is mounted inside the outer container 10. The inner container 30 includes a bottom surface 31, an inner wall 32 extending upward from the bottom surface 31, and an outer wall 33 spaced outward from the inner wall 32 by a predetermined distance.

The inner wall 32 is formed on an outer peripheral surface thereof with a coupling protrusion 321, and the coupling protrusion 321 is fitted into a coupling groove 521 formed in a fixing member 50, thereby preventing the fixing member 50 from being separated from the inner container 30.

The outer wall 33 is formed on an outer peripheral surface thereof with the coupling groove 331, and the coupling groove 331 is coupled to the coupling protrusion 13 formed on the inner peripheral surface of the outer container 10, thereby preventing the inner container 30 from being separated from the outer container 10.

The hinge bracket 34 is formed in the outer peripheral surface of the outer wall 33, and a hinge block 63 formed on the inner container lid 60 is hinged with the hinge bracket 34.

The inner container 30 is provided therein with the impregnation member 40 impregnated with the cosmetic material, and the impregnation member 40 includes at least one selected from the group consisting of Butadiene Rubber (BR), Styrene Butadiene Rubber (SBR), Natural Rubber (NR), Natural Rubber Styrene Butadiene Rubber (NRSBR), Acrylonitrile-Butadiene Rubber (NBR), wet urethane, dry urethane, polyether, polyester, polyvinyl chloride, polyethylene, latex, silicone, polyvinyl alcohol (PVA), nitrile rubber, butyl rubber, and neoprene.

As shown in FIG. 6, the impregnation member 40 includes an intaglio-pattern part 42 having an intaglio-pattern formed as the surface 41 is burned by a laser.

The intaglio-pattern part 42 may be provided in a form of a pattern or a logo on the surface 41 of the impregnation member 40, and may be provided in the form of multiple parallel lines, or in a form of a lattice pattern or an oblique pattern formed as the multiple parallel lines cross each other.

The surface 41 of the impregnation member 40 is delicately intaglio-patterned by laser machining, so that various and delicate patterns and logos may be formed. Accordingly, the cosmetic material may be easily discharged from the impregnation member 40, and the aesthetics of the impregnating member 40 may be maximized.

In addition, differently form the related art, since the intaglio-pattern is formed by the laser, the intaglio-pattern may be easily formed, and variously-shaped intaglio-patterns may be easily formed.

The intaglio-pattern part 42 has the width w in the range of 0.1 mm to 5.0 mm and the depth d in the range of 0.2 mm to 8.0 mm in order to discharge a desirable amount of cosmetic material.

If the width w is less than 0.1 mm, or the depth d is less than 0.2 mm, a small amount of cosmetic material is discharged similarly to the related art when a user applies the cosmetic material impregnated into the impregnation member 40 to a puff (P). Accordingly, it may be difficult for the user to make up.

In addition, if the width w is greater than 5.0 mm or the depth d is greater than 8.0 mm, a surficial area for the discharge of the cosmetic material is increased when the cosmetic material impregnated into the impregnation member 40 is applied to the puff P. Accordingly, an excess amount of cosmetic material is applied to the face of a user, so that the user may feel inconvenient in use.

As shown in FIG. 7, the intaglio-pattern part 42 is maintained in an open cell structure and has a section formed in an inverted triangular shape. Accordingly, when the cosmetic material impregnated into the impregnation member 40 is applied to the puff P, the user may obtain an appropriate amount of cosmetic material.

The fixing member 50 is coupled to the inner container 30, and includes a horizontally extension member 51 extending inwardly and a downward extension member 52 extending downward from the horizontally extension member 51.

The horizontally extension member 51 is mounted on an upper end of the inner wall 32 of the inner container 30 to prevent the impregnation member 40 from deviating from the inner container 30.

The downward extension member 52 is formed in an inner peripheral surface thereof with a coupling groove 521, and the coupling groove 521 is coupled to the coupling protrusion 321 formed on the outer peripheral surface of the inner wall 32 of the inner container 30, thereby preventing the fixing member 50 from deviating from the inner container 30.

The inner container 30 is provided at one side thereof with the inner container lid 60 to open or close the inner container 30.

The inner container lid 60 is formed at one side thereof with a handle 61, and formed at a lower end thereof with a sealing member 62, and a hinge block 63 is formed opposite to the handle 61.

The handle 61 facilitates the opening or closing of the inner container lid 60.

When the inner container lid 60 closes the inner container 30, the sealing member 62 is fitted into the inside of the outer wall 33 of the inner container 30 to enhance sealing.

The hinge block 63 is fitted into the hinge bracket 34 of the inner container 30 and fixed by a hinge pin 35.

Hereinafter, the assembling method and the use state of the cosmetic container including the impregnation member having the surface intaglio-patterned by laser beam machining according to one embodiment of the present invention will be described in detail.

In order to assemble the cosmetic container including the impregnation member having the surface intaglio-patterned by laser beam machining according to one embodiment of the present invention, after the outer container lid 20 is coupled to the outer container 10, the inner container lid 60 is coupled to the inner container 30.

Thereafter, the impregnation member 40 impregnated with the cosmetic material is mounted in the inner container 30 coupled to the inner container lid 60. In this case, the impregnation member 40 includes the intaglio-pattern part 42 having the intaglio-pattern formed by burning the surface 41 by the laser as shown in FIG. 6.

The intaglio-pattern part 42 may be provided in a form of a pattern or a logo on the surface 41 of the impregnation member 40, and may be provided in the form of multiple parallel lines, or in a form of a lattice pattern or an oblique pattern formed as the multiple parallel lines cross each other.

Thereafter, the fixing member 50 is coupled to the inner container 30 having the impregnation member 40 therein, and then the inner container 30 is coupled to the inside of the outer container 10 to complete the assembling work.

In the assembled cosmetic container including the impregnation member having the surface intaglio-patterned by laser beam machining, the surface 41 of the impregnation member 40 is subject to the laser beam machining to be delicately intaglio-patterned, so that free and delicate patterns may be realized, the cosmetic material may be easily discharged from the impregnation member 40, and various and delicate logos may be formed, so that the aesthetics of the impregnating member 40 may be maximized. In addition, since the intaglio-pattern may be formed using a laser differently from the related art, variously-shaped intaglio-patterns may be easily formed.

As shown in FIG. 7, the intaglio-pattern part 42 is maintained in an open cell structure and has a section formed in an inverted triangular shape. Accordingly, when the cosmetic material impregnated into the impregnation member 40 is applied to the puff P, the user may obtain an appropriate amount of cosmetic material.

Embodiment 1

The following experimental manner was used in order to estimate whether a user may use a cosmetic material remaining on a top surface of the impregnation member using a puff at next time when a user uses cosmetics having an impregnation member using the puff.

When an impregnation member having a surface not intaglio-patterned (comparative example 1), an impregnation member having a surface intaglio-patterned by pressing (comparative example 2), and an impregnation member having a surface intaglio-patterned by laser beam machining (comparative example 3) were repeatedly pressed three times, amounts of cosmetic material remaining on the top surfaces of the impregnation members were compared with one another. Hereinafter, the experimental manner will be described below.

The puff to be applied with cosmetic material was placed on press machine to press samples under the conditions of the same depth, the same area, and the same force, cosmetic material was impregnated into the impregnation members (comparative examples 1 to 3) in the same size, and the impregnation members were pressed under the same pressure of 0.4 kgf/m for one second at three times. In this case, an amount of cosmetic material remaining on the top surface of each impregnation member was measured five times, and the measurement unit was gram (g).

TABLE 1

| | Experimental number | | | | |
|---|---|---|---|---|---|
| | $1^{st}$ | $2^{nd}$ | $3^{rd}$ | $4^{th}$ | $5^{th}$ |
| Comparative example 1 | 0.14 | 0.12 | 0.11 | 0.12 | 0.11 |
| Comparative example 2 | 0.06 | 0.07 | 0.05 | 0.04 | 0.05 |
| Comparative example 3 | 0.21 | 0.20 | 0.18 | 0.20 | 0.19 |

As shown in Table 1, when the impregnation members was pressed by a puff, the amounts of cosmetic material remaining on the top surfaces of the impregnation members were increased in the order of the comparative examples 1, 2, and 3 (the impregnation member having the surface not intaglio-patterned, the impregnation member having the surface intaglio-patterned by pressing, and the impregnation member having a surface intaglio-patterned by laser beam machining).

In the case of the comparative example 3, since the intaglio-pattern part 42 maintained in the open cell structure is formed on the top surface of the impregnation member by a laser, if the impregnation member is pressed by the puff, the cosmetic material present at a lower portion of the impregnation member is discharged to the top surface and collected inside the intaglio-pattern part 42, and a large amount of cosmetic material remains on the top surface of the impregnation member due to the surface tension.

On the contrary, in the case of the comparative example 2, since the intaglio-pattern is not formed on the top surface of the impregnation member, if the impregnation member is pressed by the puff, the discharged cosmetic material remains in smaller amount on the top surface of the impregnation member. In the case of comparative example 2, since the intaglio-pattern is formed in a close cell structure on the top surface of the impregnation member by thermal compression, if the impregnation member is pressed by the puff, not only are a smaller amount of cosmetic material discharged to the top surface of the impregnation member, but the smallest amount of cosmetic material remains on the top surface of the impregnation member.

As a result, in the cases of the impregnation member having the surface not intaglio-patterned (comparative example 1) and the impregnation member having the surface intaglio-patterned by pressing (comparative example 2), cosmetic material is discharged to the top surface of the impregnation member and then smaller amounts of cosmetic material remains on the top surface of the impregnation member. In the case of the impregnation member having the surface intaglio-patterned by laser beam machining (comparative example 3) according to the present invention, the cosmetic material is collected into the intaglio-pattern part 42 formed on the top surface of the impregnation member, so that a larger amount of cosmetic material remains on the impregnation member.

Embodiment 2

After an impregnation member having a surface not intaglio-patterned (comparative example 1), an impregnation member having a surface intaglio-patterned by pressing (comparative example 2), and an impregnation member having a surface intaglio-patterned by laser beam machining (comparative example 3) were impregnated with cosmetic material, 20 women aged 20-30 were allowed to use each of the impregnation members for 6 weeks using puffs. The use feelings of the cosmetic material in the above cases were compared using qualitative data, and the average values are shown in Table 2 below. The evaluation were performed based on the easiness in discharging cosmetic material and the consistency of cosmetic convenience, and the evaluation indexes were as follows (0-1: very bad, 1-2: bad, 2-3: general, 3-4: excellent, 4-5: very excellent)

TABLE 2

|  | Comparative example 1 | Comparative example 2 | Comparative example 3 |
|---|---|---|---|
| $1^{st}$ week | 4.2 | 3.8 | 4.7 |
| $2^{nd}$ week | 3.7 | 3.3 | 4.4 |
| $3^{rd}$ week | 3.2 | 2.7 | 4.0 |
| $4^{th}$ week | 2.4 | 2.0 | 3.8 |
| $5^{th}$ week | 1.2 | 1.1 | 3.4 |
| $6^{th}$ week | 0.3 | 0.2 | 3.2 |

As shown in table 2, in the cases of the impregnation member having the surface not intaglio-patterned (comparative example 1), and the impregnation member having the surface intaglio-patterned by pressing (comparative example 2), as the use period of the impregnation member is increased, the satisfaction for the cosmetics is remarkably decreased according to the evaluation. This is because the amount of discharged cosmetics are more sharply reduced toward the ending stage of use from the early stage of the use and the cosmetic material is not uniformly discharged, so that the consistency of cosmetic convenience is degraded according to the evaluation of the users.

However, in the case of the comparative example 3 (the impregnation member having a surface intaglio-patterned by laser beam machining), although the use period of the impregnation member elapses, the significant change is not made in the amount of discharged cosmetics, which maintain the satisfaction of the users.

As a result, according to the embodiment 2, in the cases of the impregnation member having the surface not intaglio-patterned (comparative example 1), and the impregnation member having the surface intaglio-patterned by pressing (comparative example 2), as the impregnation member is used, the cosmetic material present in the upper portion of the impregnation member is depleted and the cosmetic material present in the lower portion of the impregnation member is sunken to the lower portion of the impregnation member, so that the amount of discharged cosmetic material is reduced, which decreases the satisfaction of the users. On the contrary, in the case of the impregnation member having the surface intaglio-patterned by laser beam machining (comparative example 3), even if the impregnation member is used for a long term, the cosmetic material is lifted to the top surface of the impregnation member, the amount of discharged cosmetic material is not sharply reduced, and the cosmetic material is uniformly discharged. Accordingly, the excellent consistency of cosmetic convenience may be represented, and relatively higher satisfaction may be obtained.

Embodiment 3

As described in embodiments 1 and 2, the impregnation member having the surface intaglio-patterned by the laser according to the present invention represents excellent performance in an amount of discharged cosmetic material and the consistency of cosmetic convenience.

Accordingly, when machining the impregnation having the surface intaglio-patterned by the laser according to the present invention, various widths w and various depths d are formed in the surfaces of impregnation members by using a laser in order to determine the width w and the depth d of the most usable intaglio-pattern, and then cosmetic material is impregnated into the impregnation members. The impregnation members are pressed under the same pressure of 0.4 kgf/cm² to measure an amount of cosmetic material remaining on the top surface of the impregnation member, and the unit is g.

TABLE 3

|  | Depth (d) | Width (w) | Amount of cosmetic material remaining on top surface of the impregnation member |
|---|---|---|---|
| Comparative example 1 | 2.0 mm | 0.05 mm | 0.11 |
| Comparative example 2 | 2.0 mm | 0.1 mm | 0.18 |
| Comparative example 3 | 2.0 mm | 2.5 mm | 0.23 |
| Comparative example 4 | 2.0 mm | 5.0 mm | 0.20 |
| Comparative example 5 | 2.0 mm | 6.0 mm | 0.10 |

An amount of cosmetic material remaining on the top surface of the impregnation member was measured while changing the width w in the state that the depth d of the laser-intaglio-pattern formed on the surface of the impregnation member is fixed.

As shown in Table 3, when the width w of the laser-intaglio-pattern formed on the surface of the impregnation member is less than 0.05 mm (comparative example 1), the width w is significantly narrowed while approximating the size of the foaming cell of the impregnation member. Accordingly, similarly to the impregnation member having the top surface not intaglio-patterned, the surface tension is not generated from the cosmetic material remaining on the top surface of the impregnation member.

In addition, when the width w of the laser-intaglio-pattern formed on the surface of the impregnation member exceeds 6.0 mm (comparative example 5), the width w is significantly widened, so that the surface tension is not generated from the cosmetic material remaining on the top surface of the impregnation member similarly to the impregnation member having the surface not intaglio-patterned.

Meanwhile, when the width w of the laser-intaglio-pattern formed on the surface of the impregnation ember is in the range of 0.1 mm to 5.0 mm (comparative examples 2 to 4), a larger amount of cosmetic material remains on the top surface of the impregnation member. Especially, when the width w is 2.5 mm (comparative example 3), the largest amount of cosmetic material remains on the top surface of the impregnation member. Accordingly, when a user uses the cosmetic material using a puff, the cosmetic material is uniformly discharged, so that the consistency of cosmetic convenience is excellently represented, and thus the satisfaction of the user is increased.

Accordingly, it can be recognized that the surface tension is generated from foundation cosmetic material having viscosity when the width w of the intaglio-pattern is in the range of 0.1 mm to 5.0 mm.

Embodiment 4

As described in embodiment 3, when the width w of the laser-intaglio-pattern formed on the surface of the impregnation member is 2.5 mm, the largest amount of cosmetic material remains on the tops surface of the impregnation member. In order to determine the depth d of the laser-intaglio-pattern to discharge an appropriate amount of cosmetic material and to represent the excellent consistency of cosmetic convenience in the state of the width w of the laser-intaglio-pattern formed on the surface of the impregnation member is fixed to 2.5 mm, an amount of cosmetic material remaining on the top surface of the impregnation member was measured while changing the depth d of the laser-intaglio-pattern. The unit is g.

TABLE 4

|  | Depth (d) | Width (w) | Amount of cosmetic material remaining on top surface of the impregnation member |
|---|---|---|---|
| Comparative example 1 | 2.5 mm | 0.1 mm | 0.10 |
| Comparative example 2 | 2.5 mm | 0.2 mm | 0.20 |
| Comparative example 3 | 2.5 mm | 4.0 mm | 0.24 |
| Comparative example 4 | 2.5 mm | 8.0 mm | 0.21 |
| Comparative example 5 | 2.5 mm | 10.0 mm | 0.09 |

As shown in Table 4, when the depth d formed on the surface of the impregnation member is less than 0.1 mm (comparative example 1), the thin depth d does not generate the surface tension from the cosmetic material remaining on the top surface of the impregnation member similarly to the impregnation member having the surface not intaglio-patterned. When the depth d formed on the surface of the impregnation member exceeds 10.0 mm (comparative example 5), the deep depth d sinks down the cosmetic material discharged to the top surface of the impregnation member due to gravity. Accordingly, a smaller amount of cosmetic material remains on the top surface of the impregnation member.

On the contrary, when the depth d formed on the surface of the impregnation member is in the range of 0.2 mm to 8.0 mm (comparative examples 2 to 4), a larger amount of cosmetic material remains on the top surface of the impregnation member. Particularly, when the depth d is 4.0 mm (comparative example 3), the largest amount of cosmetic material remains on the top surface of the impregnation member. Accordingly, when a user wears the cosmetic materials using a puff, the cosmetic material is uniformly discharged, so that the excellent consistency of cosmetic convenience is represented, so the satisfaction of consumers is increased.

As a result, it can be recognized that, when the laser-intaglio-pattern formed on the surface of the impregnation member has the width w in the range of 0.1 mm to 5.0 mm and the depth d in the range of 0.2 mm to 8.0 mm, the largest amount of cosmetic material remains on the top surface of the impregnation member. The above ranges generate the surface tension from the foundation cosmetic material having viscosity, so that the easiness in discharging cosmetic material and the consistency of cosmetic convenience can be improved.

Although a cosmetic container including an impregnation member having a surface intaglio-patterned by laser beam machining according to one embodiment of the present invention has been described for illustrative purposes, the person skilled in the art will appreciate that various modifications, additions and substitutions are possible, without departing from the scope and spirit of the invention as disclosed in the accompanying claims.

DESCRIPTION OF REFERENCE NUMERALS 10. outer container
11. Pressing button
12. locking step
13. coupling protrusion
14. hinge bracket mounting groove
20. outer container lid
21. locking protrusion
30. inner container
31. bottom surface
32. inner wall
321. coupling protrusion
33. outer wall
331. coupling groove
34. hinge bracket
35. hinge pin
40. impregnation member
41. surface
42. intaglio-pattern part
50. fixing member
51. horizontally extensor member
52. downward extension member
521. coupling groove
60. inner container lid
61. Handle
62. sealing member
63. hinge block

What is claimed is:

1. A cosmetic container including an impregnation member having a surface on which an intaglio-pattern groove is formed, the cosmetic container comprising:
the intaglio-pattern groove (42) having an intaglio pattern formed as the surface (41) of the impregnation member (40) is burned by a laser such that an open cell structure of the surface (41) of the impregnation member (40) is maintained,
wherein the intaglio-pattern groove (42) has a width (w) that is ≥2.5 mm and less than 5.0 mm, wherein the intaglio-pattern groove (42) has a depth (d) more than 1.0 mm and less than 8.0 mm, wherein the impregnation member (40) having the intaglio-pattern groove (42) formed on the surface (41) thereof is impregnated with cosmetic material, wherein the intaglio-pattern groove (42) is formed on the surface (41) of the impregnation member (40) and formed in a form of lines, or in a form of a lattice pattern or an oblique pattern formed as the lines cross each other, wherein the intaglio-pattern groove (42) has a cross-section formed in an inverted triangle shape while maintaining the open cell structure, and wherein when the impregnation member (40) is pressed, the cosmetic material present at a lower portion of the impregnation member (40) is discharged to a top surface of the impregnation member (40) and collected inside the intaglio-pattern groove (42), and the cosmetic material remains on the top surface of the impregnation member (40) due to surface tension.

2. A cosmetic container including an impregnation member having a surface on which an intaglio-pattern groove is formed, the cosmetic container comprising:

an outer container (10) having an upper portion that is open;

an outer container lid (20) coupled to one side of the outer container (10);

an inner container (30) mounted inside the outer container (10);

the impregnation member (40) mounted in the inner container (30) and impregnated with cosmetic material; and an inner container lid (60) hinged with one side of the inner container (30) to be open or closed, wherein the impregnation member (40) includes the intaglio-pattern groove (42) having an intaglio-pattern formed as the surface (41) is burned by a laser such that an open cell structure of the surface (41) of the impregnation member (40) is maintained, wherein the intaglio-pattern groove (42) has a width (w) that is ≥2.5 mm and less than 5.0 mm, wherein the intaglio-pattern groove (42) has a depth (d) more than 1.0 mm and less than 8.0 mm, wherein the intaglio-pattern groove (42) is formed on the surface (41) of the impregnation member (40) and formed in a form of lines, or in a form of a lattice pattern or an oblique pattern formed as the lines cross each other, wherein the intaglio-pattern groove (42) has a cross-section formed in an inverted triangle shape while maintaining the open cell structure, and wherein when the impregnation member (40) is pressed, the cosmetic material present at a lower portion of the impregnation member (40) is discharged to a top surface of the impregnation member (40) and collected inside the intaglio-pattern groove (42), and the cosmetic material remains on the top surface of the impregnation member (40) due to surface tension.

3. A cosmetic container including an impregnation member having a surface on which an intaglio-pattern groove is formed, the cosmetic container comprising:

an inner container (30);

the impregnation member (40) mounted in the inner container (30) and impregnated with cosmetic material; and an inner container lid (60) hinged with one side of the inner container (30) to be open or closed, wherein the impregnation member (40) includes the intaglio-pattern groove (42) having an intaglio pattern formed as the surface (41) is burned by a laser such that an open cell structure of the surface (41) of the impregnation member (40) is maintained, wherein the intaglio-pattern groove (42) has a width (w) that is ≥2.5 mm and less than 5.0 mm, wherein the intaglio-pattern groove (42) has a depth (d) more than 1.0 mm and less than 8.0 mm, wherein the intaglio-pattern groove (42) is formed on the surface (41) of the impregnation member (40) and formed in a form of lines, or in a form of a lattice pattern or an oblique pattern formed as the lines cross each other, wherein the intaglio-pattern groove (42) has a cross-section formed in an inverted triangle shape while maintaining the open cell structure, and wherein when the impregnation member (40) is pressed, the cosmetic material present at a lower portion of the impregnation member (40) is discharged to a top surface of the impregnation member (40) and collected inside the intaglio-pattern groove (42), and the cosmetic material remains on the top surface of the impregnation member (40) due to surface tension.

4. The cosmetic container of claim 2, further comprising a fixing member (50) coupled to an upper end of the inner container (30) to prevent the impregnation member (40) from deviating out of the inner container (30).

5. The cosmetic container of claim 1, wherein the intaglio-pattern groove (42) is provided in a form of a pattern or a logo on the surface (41) of the impregnation member (40).

6. The cosmetic container of claim 3, further comprising a fixing member (50) coupled to an upper end of the inner container (30) to prevent the impregnation member (40) from deviating out of the inner container (30).

7. The cosmetic container of claim 2, wherein the intaglio-pattern groove (42) is provided in a form of a pattern or a logo on the surface (41) of the impregnation member (40).

8. The cosmetic container of claim 3, wherein the intaglio-pattern groove (42) is provided in a form of a pattern or a logo on the surface (41) of the impregnation member (40).

* * * * *